United States Patent

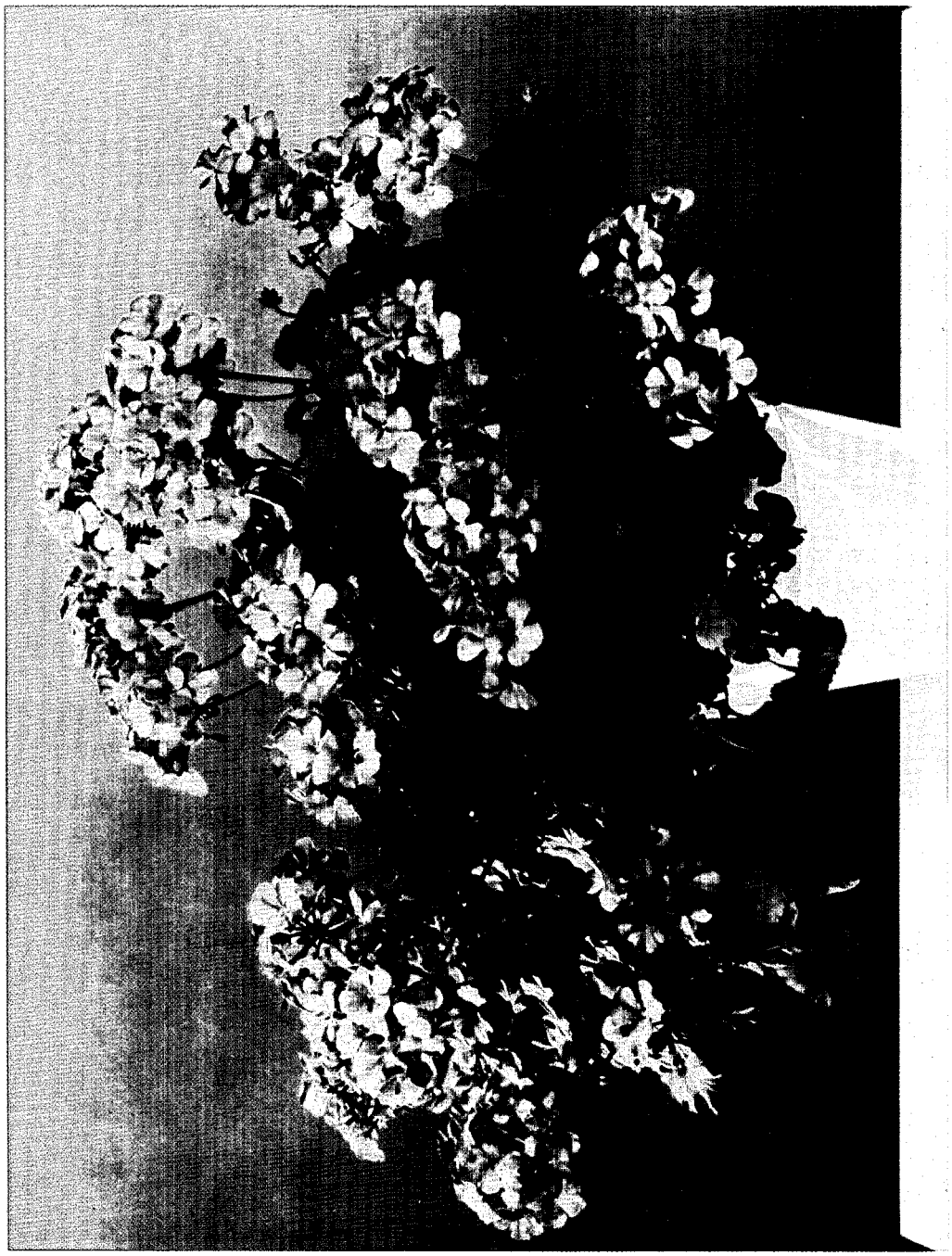

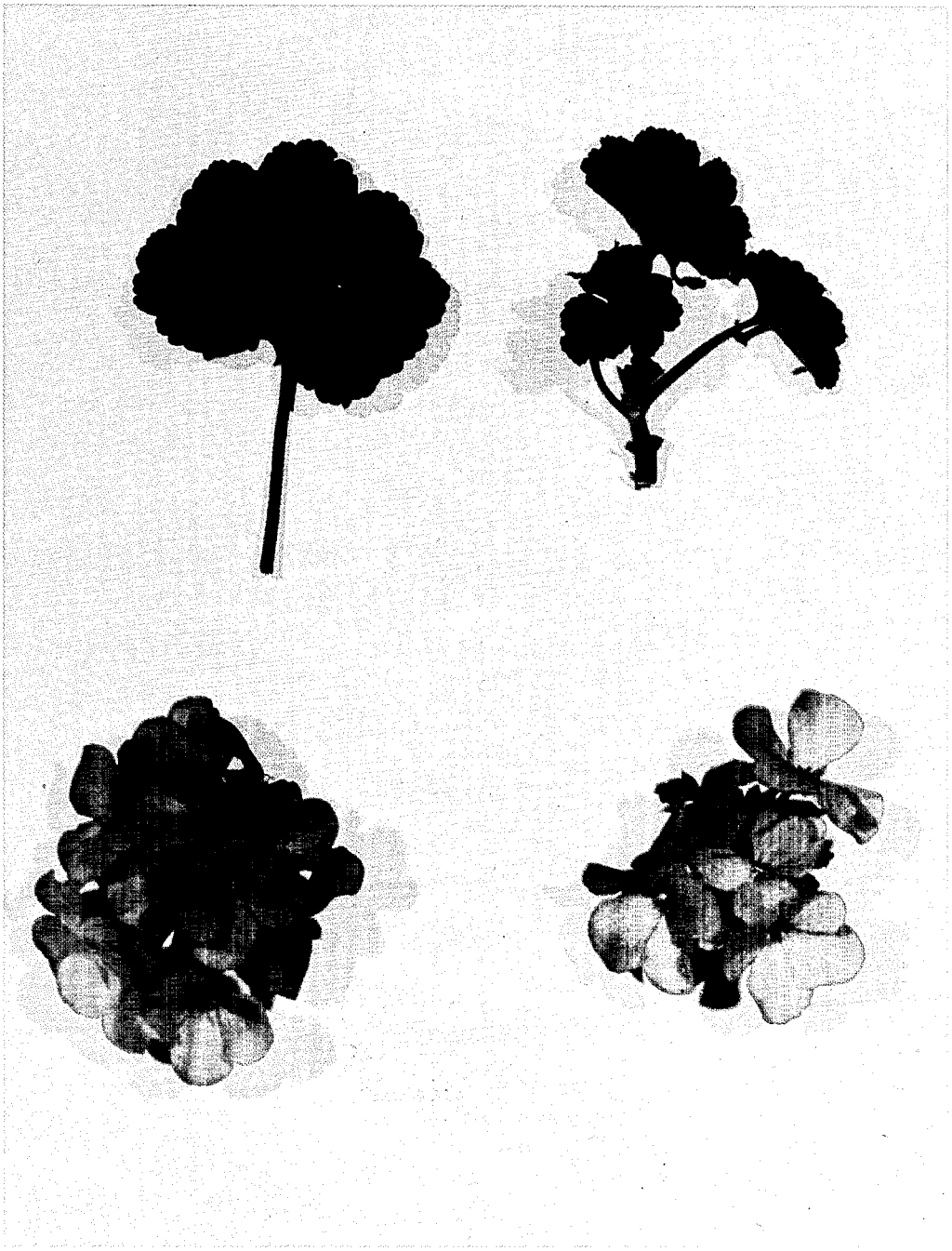

Plant Pat. 3,941

Patented Aug. 24, 1976

3,941

GERANIUM PLANT

William E. Duffett, Akron, Ohio, and Walter W. Knicely, Inwood, W. Va., assignors to Yoder Brothers, Inc., Barberton, Ohio Filed June 20, 1975, Ser. No. 588,941

Int. Cl.[2] A01H 5/00

U.S. Cl. Plt.—68 1 Claim

The present invention comprises a new and distinct cultivar, a hybrid of the genus Pelargonium, L'Her., hereinafter referred to by the cultivar name Happy Cherub (#69061004).

Happy Cherub was originated from a cross made under the supervision of William E. Duffett and Walter W. Knicely in a controlled breeding program in Barberton, Ohio in the year 1968.

The female, or seed parent, was #651223–1 (unnamed seedling), a single of light pink color. The male, or pollen parent, was #671356–4 (unnamed seedling), a single of pink color. Both parents were products of the breeding program of the present inventors.

Happy Cherub was discovered and selected as a flowering seedling within the progeny of the stated cross by William E. Duffett and Walter W. Knicely on Sept. 26, 1969 in an outdoor field environment in Barberton, Ohio.

Happy Cherub is a product of a planned breeding program which had the objective of creating durable, disease tolerant geraniums that would fulfill in part or in whole the need for a geranium with compact and spreading growth habit, vibrant flower color, fast spring pot response period, and prolific flowering traits under outdoor summer conditions in Ohio.

The first act of asexual reproduction of Happy Cherub was accomplished when vegetative cuttings were taken from the initial selection in September 1969, in Barberton, Ohio, by a technician under formulations established and supervised by William E. Duffett and Walter W. Knicely.

Continued asexual reproduction by vegetative cuttings for evaluated tests in flowering and stock programs in conjunction with horticultural certification initiated Sept. 23, 1970, by William E. Duffett and Walter W. Knicely have demonstrated that the combination of characteristics as herein disclosed for Happy Cherub are firmly fixed and are retained through successive generations of asexual reproduction.

The following descriptive observations, measurements, and comparisons were derived from plants grown both in a greenhouse and under outdoor field conditions. The greenhouse-grown, spring flowering containerized plants were planted in an outdoor filed in late May, early June and observed during the summer and fall months. The environmental conditions under which the observed plants were grown are generally described in Local Climatological Data, Akron, Ohio, U.S. Department of Commerce, National Oceanic and Atmospheric Administration, Data Service, Washington, D.C., 1970, 1971, 1972, 1973, 1974. General cultural practices utilized closely approximate those generally used in commercial practice and are described in Chart A, attached at the end of the present specification.

The following traits have been repeatedly observed and are determined to be basic characteristics of Happy Cherub which in combination distinguish this geranium as a new and distinct cultivar:

(1) Coral rose flower color with minimal color fade.

(2) Compact, spreading growth habit.

(3) Prolific flowering traits under Ohio outdoor summer conditions.

(4) Durable flower and foliage under Ohio outdoor summer conditions.

(5) Fast spring pot flowering response.

The accompanying photographic drawings show typical flower and foliage characteristics of Happy Cherub. Sheet 1 illustrates Happy Cherub in bloom and Sheet 2 comprises a photograph showing the development of the inflorescence and the foliage of Happy Cherub. It is noted that difficulty was encountered in obtaining photographs accurately representing the true colors of Happy Cherub. The actual flower color of Happy Cherub is closely represented in Sheet 1 and the true foliage color is closely represented in Sheet 2. The color readings are, however, correct.

The phenotype of Happy Cherub may vary significantly with variations in environment such as temperature, light intensity, and daylength. The genotype of Happy Cherub was not observed under all possible environments.

Of the many commercially available cultivars known to the present inventors, the most similar cultivars in comparison to Happy Cherub are Quest (unpatented) and Sincerity (unpatented). Reference is made to attached Chart B which compares certain characteristics of Happy Cherub and the noted cultivars. General comparisons are as follows:

(1) In comparison to Quest, Happy Cherub has rose pink flower color with more red and less salmon tones, a shorter height, shorter spring flowering response period, and more prolific flowering traits under outdoor summer Ohio conditions. The semi-spreading growth habit and the outdoor flower and foliage durability under summer Ohio conditions of Happy Cherub are similar to those of Quest.

(2) In comparison to Sincerity, Happy Cherub has rose pink flower color, a more spreading growth habit, shorter height, shorter spring flowering response period, and more prolific flowering traits under outdoor summer Ohio conditions. The outdoor flower and foliage durability under summer Ohio conditions of Happy Cherub are similar to those of Sincerity.

In the following description, color references are to the Munsell Limit Color Cascade, 1972 edition. Color values were determined between 4:00 p.m. and 4:30 p.m. on July 24, 1974, under 150 foot candle light intensity at Barberton, Ohio.

BOTANICAL CLASSIFICATION

A hybrid of the genus Pelargonium, L'Her., cv Happy Cherub.

I. Inflorescence

A. Umbel:

*Average Diameter.*—3.0 inches.

*Average depth.*—2.3 inches.

*Peduncle.*—Ranges from 3 inches to 5.7 inches in length, averaging 4.0 inches.

*Pedicel.*—0.8 inches to 1.2 inches in length.

B. Corolla:

*Average diameter.*—1.5 inches.

*Type.*—Single; rotate.

*Color.*—Abaxial: Between 39–8 and 40–9 with less vibrance and more blue tones. Adaxial: 40–6 with less vibrance and more blue tones.

C. Bud:

*Shape.*—Conodial.

*Color.*—Abaxial: 37–7. Adaxial: 39–8.

D. Reproductive organs:

*Androecium.*—Stamen: Monodelphous; dorsifixed; pentadynamous. Pollen: Present.

*Gynoecium.*—Stigma: 5-lobed; linear. Carpel: 5 locules; pubescent.

E. Response period: Early. 80% of plants in plot had at least 1 flower open on May 30, 1974 from a direct stick date of Apr. 3, 1974 (8 weeks).

F. Production: Good.

| Date: | Average number of flowers per plant |
|---|---|
| July 15, 1974 | 2.4 |
| Aug. 1, 1974 | 3.5 |
| Aug. 15, 1974 | 4.4 |
| Sept. 1, 1974 | 3.5 |

G. Durability:

*Shatter resistance.*—Good.

*Tolerance of botrytis.*—Good.

II. Plant

A. Foliage:

*Form.*—Reni-form.

*Margin.*—Undulate; crenate.

*Color.*—Abaxial: Between 21–13 and 21–14. Adaxial: Approximately 21–15 but overlaid with grey. Zonation: Approximately 32–15 but with more grey.

*Durability (outdoor).*—Good.

B. Growth habit:

*Form.*—Semi-spreading.

*Height.*—Short, semi-dwarf.

*Internode length.*—Short.

C. Durability:

*Tolerance of botrytis.*—Good.

CHART A—ENVIRONMENTS FOR GERANIUM PERFORMANCE EVALUATION COMMONLY USED IN BARBERTON, OHIO

| | Environment | |
|---|---|---|
| | I. Greenhouse | II. Outdoor field |
| Period of year | April through May | June through September |
| Temperature (° F.) | Night: 62–65; Bright day: 72–75; Cloudy day: 68–70 | Uncontrolled dependent upon prevailing weather conditions. |
| Light | Uncontrolled dependent upon natural daylength and light intensity. Light shade compound on greenhouse class. | Uncontrolled dependent on natural daylength and light intensity. |
| Schedule and specifications | Take vegetative cutting: April 2. Cutting specifications: 2–2.75 inches in length. Direct stick: April 3; 1 cutting per 4 inch plastic pot. Media: 1 part soil, 1 part peat, 1 part perlite. Move to 6″ x 7″ spacing: April 23. Flower date: May 28. | Plant: early June (product produced in I). Location: outdoor field. Media: well drained field soil. |

CHART B—COMPARISON OF HAPPY CHERUB WITH QUEST AND SINCERITY

| Cultivar | Flower color | Growth habit | Height | Spring flowering response period | Outdoor flower production | Outdoor flower durability | Outdoor foliage durability |
|---|---|---|---|---|---|---|---|
| Happy Cherub | Rose pink | Semi-spreading | Semi-dwarf | Early | Prolific | Good | Good. |
| Quest | do | do | Tall | Late | Poor | do | Do. |
| Sincerity | Scarlet orange | Semi-upright | do | do | Medium | do | Do. |

NOTE.—Comparisons made of plants grown in a greenhouse and in an outdoor field in Barberton, Ohio, under cultural conditions as described in Chart A.

We claim:

1. A new and distinct cultivator of geranium plant characterized particularly as to uniqueness by the combined characteristics of coral rose flower color with minimal color fade, compact, spreading growth habit, prolific flowering traits under Ohio outdoor summer conditions, durable flower and foliage under Ohio outdoor summer conditions, and fast spring pot flowering response.

No references cited.

ROBERT E. BAGWILL, Primary Examiner